United States Patent [19]
Ng et al.

[11] Patent Number: 5,199,298
[45] Date of Patent: Apr. 6, 1993

[54] WALL SHEAR STRESS SENSOR

[75] Inventors: Kay Y. Ng, Kuala Kumpur, Malaysia; Martin A. Schmidt, Reading, Mass.

[73] Assignee: Massachusetts Institute of Technology, Cambridge, Mass.

[21] Appl. No.: 718,786

[22] Filed: Jun. 21, 1991

[51] Int. Cl.$^5$ ............................................. G01N 11/00
[52] U.S. Cl. ...................................... 73/54.01; 73/147
[58] Field of Search ...................... 73/774, 777, 54.01, 73/861.71, 861.73, 147, 54.01

[56] References Cited

U.S. PATENT DOCUMENTS

| | | | |
|---|---|---|---|
| 4,781,070 | 11/1988 | Derin | 73/861.71 |
| 4,896,098 | 1/1990 | Haritonidis et al. | 324/663 |
| 4,908,693 | 3/1990 | Nishiguchi | 73/777 |
| 4,926,682 | 5/1990 | Holm-Kennedy et al. | 73/54.01 |

OTHER PUBLICATIONS

"A Liquid Shear-Stress Sensor Fabricated Using Wafer Bonding Technology", by Kay Yip Ng et al., presented at the IEEE *Transducers* '91 Conference, San Francisco, Calif., Jun. 23-30, 1991, pp.1–4.

*Primary Examiner*—Robert Raevis
*Attorney, Agent, or Firm*—Hamilton, Brook, Smith & Reynolds

[57] ABSTRACT

A shear stress sensor is fabricated using wafer bonding technology. The shear stress sensor is a floating element shear stress sensor designed to measure shear stresses of about 1 kPa–100 kPa over a wide range of operating conditions (temperature, humidity), as well as for a large variety of fluids. The sensor employs a silicon plate suspended about 1.4 microns above the surface of a silicon substrate by piezoresistive arms. The arms are directed parallel to the flow of interest and are loaded in tensile or compressive stress. The piezoresistive arms convert the strain to an electrical output which can be configured in a half bridge circuit with appropriate wiring. Fabrication of the sensor includes bonding a substrate silicon wafer and a device wafer which has an epitaxial silicon layer grown on top of a p+ dopant layer. The device wafer is etched back using the p+ layer as an etch stop. After selective removable of the p+ layer, ohmic contacts are formed through implantation and metalization techniques. Plasma etching of the epitaxial silicon layer releases the sensor plate. A PECVD oxide is used to define the geometric characteristics of the plate and arms and to passivate the wafer chip.

8 Claims, 7 Drawing Sheets

WALL SHEAR STRESS SENSOR

BACKGROUND OF THE INVENTION

There are many processes in the food and plastics industries where a measurement of the shear stress generated by a flowing fluid would provide valuable information for automated process control. As an example, in a reaction extrusion process, the shear stress generated on the inside wall of the extruder would provide a measurement of the material viscosity, and hence an indication of the state of reaction in the process. Such a liquid shear stress sensor for applications in a commercial extruder requires measurements at high shear stress (100 kPa), high pressure (5,000 psi), and high temperature (300° C.).

A variety of techniques exist for the measurement of wall shear stress including the Preston tube, Stanton tube, Sublayer fence, thermal methods and direct measurement techniques. In a pressure sensing tube, such as the Preston tube, pressure is sensed as a function of the non-dimensional velocity profile. The velocity profile is rendered non-dimensional using the wall shear stress. Thus, the measured pressure can be directly related to the wall shear stress. This method, however, depends on knowledge of the velocity profile which can be assumed known only in a limited number of cases.

The usefulness of a direct measurement has motivated a variety of shear stress sensors known as floating element balances or floating element sensors. Such sensors include a plate positioned in an opening in the sample wall and supported on a pedestal. An electric coil or force is used to reposition the shearing plate to equilibrium. The current in the coil or the force used in recentering the plate serves as a measurement of the amount of average shear stress experienced by the element. However, this method usually does not allow for the measuring of fluctuating shear stress, and only measures relatively large shear stress. Further disadvantages in this approach have been problems with pressure gradient across the floating element, fluid flow through the gap area which produces apparent and erroneous forces, communication with ambient due to the large gap, and scale resolution.

One such floating element shear stress sensor is disclosed in U.S. Pat. No. 4,896,098 by Haritonidis et al., issued Jan. 23, 1990. That shear stress sensor employs a microdimensioned plate suspended above a substrate by microdimensioned arms or tethers. The microdimensions render an extremely small shear stress sensor which substantially reduces the problems of pressure gradient across the floating element (plate), gap flow and scale resolution. The sensor also enables the resolving of very small turbulent scales. Further, the plate is suspended at a height above the substrate which forms a very small passage or cavity between the plate and substrate. The dimensions of the passageway are so small that movement of the plate by forces due to vibration is heavily dampened by a viscous damping within the passageway. The dimensions of the plate and the damping effect of the passageway enable the microdimensioned sensor to be substantially insensitive to normal forces yet very sensitive to shear forces acting on it. Read out means which are also insensitive to vertical movement are incorporated in the sensor to provide an indication of sensed shear stress.

In the preferred embodiment of U.S. Pat. No. 4,896,098, the read out means employs a conducting layer associated with the sensor plate. The conducting layer is part of an integrated differential capacitance measuring circuit which produces the sensor read out. Such read out means are not suitable for measuring shear stress in elevated temperatures or in a liquid environment. Thus, the floating element shear stress sensor of U.S. Pat. No. 4,896,098 is limited in application depending on the read out means employed.

Other shear stress sensor methods only measure forces in an air fluid or a water fluid but not both. Some methods are dependent on gravity and thus only work on a horizontal target surface. Furthermore most methods are hard to install, may disturb the flow of the fluid, and are expensive.

SUMMARY OF THE INVENTION

The present invention provides a shear stress sensor which overcomes the problems of the prior art. In particular the present invention provides a floating element shear stress sensor which is suitable for measuring shear stress in elevated temperatures and in liquid environments.

In a preferred embodiment of the present invention a wall shear stress sensor employs a plate having micron dimensions and a plurality of piezoresistive supporting arms. The arms are coupled to the plate in a manner such that the arms suspend the plate in a plane flush with a wall or surface of interest and above a substrate surface. Each arm has a longitudinal axis parallel to the axis along which fluid flows over the plate and subject wall. In response to fluid flowing over the subject wall displacing the plate, the arms become strained and provide an indication of deflection of the plate along the longitudinal axis of the arms. Readout means are coupled to the plate and arms to receive the indication of plate deflection. The readout means provide from the indication of plate deflection, measurements of detected shear stress.

The piezoresistive supporting arms are effectively insensitive to displacement of the plate along axes transverse to the longitudinal axes of the arms. To that end, the readout means provide measurements of shear stress substantially independent of forces acting along axes perpendicular to the longitudinal axes of the arms.

In accordance with one aspect of the present invention the piezoresistive supporting arms are formed of single crystal silicon. Further, the piezoresistive arms are dielectrically isolated such that the arms provide indications of plate deflection in fluid temperatures up to about 300° C.

In accordance with another aspect of the present invention the plate and arms are fabricated by a process involving silicon wafer (fusion) bonding. In that process a cavity is etched into a front surface of a first silicon wafer. A front side of a second silicon wafer is then bonded to the front surface of the first silicon wafer using silicon wafer bonding techniques. The two wafers are bonded to each other in a manner such that a portion of the front side of the second silicon wafer faces the cavity etched into the first silicon wafer. The second wafer is then thinned from the backside toward the front side to form a working layer suspended across the cavity in the first silicon wafer. The plate and arms are formed (i.e., patterned and etched) in the working layer in a manner such that the arms suspend the plate over the cavity in the first silicon wafer.

In another aspect of the present invention the working layer formed from the thinned second silicon wafer includes a single crystal silicon epitaxial layer carried on the front side of the second silicon wafer. It is from this epitaxial layer that the piezoresistive arms are formed.

In another aspect of the present invention the readout means include electrical interconnects coupled to the plate and piezoresistive arms in a bridge or half bridge configuration.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENT

Figure 1:
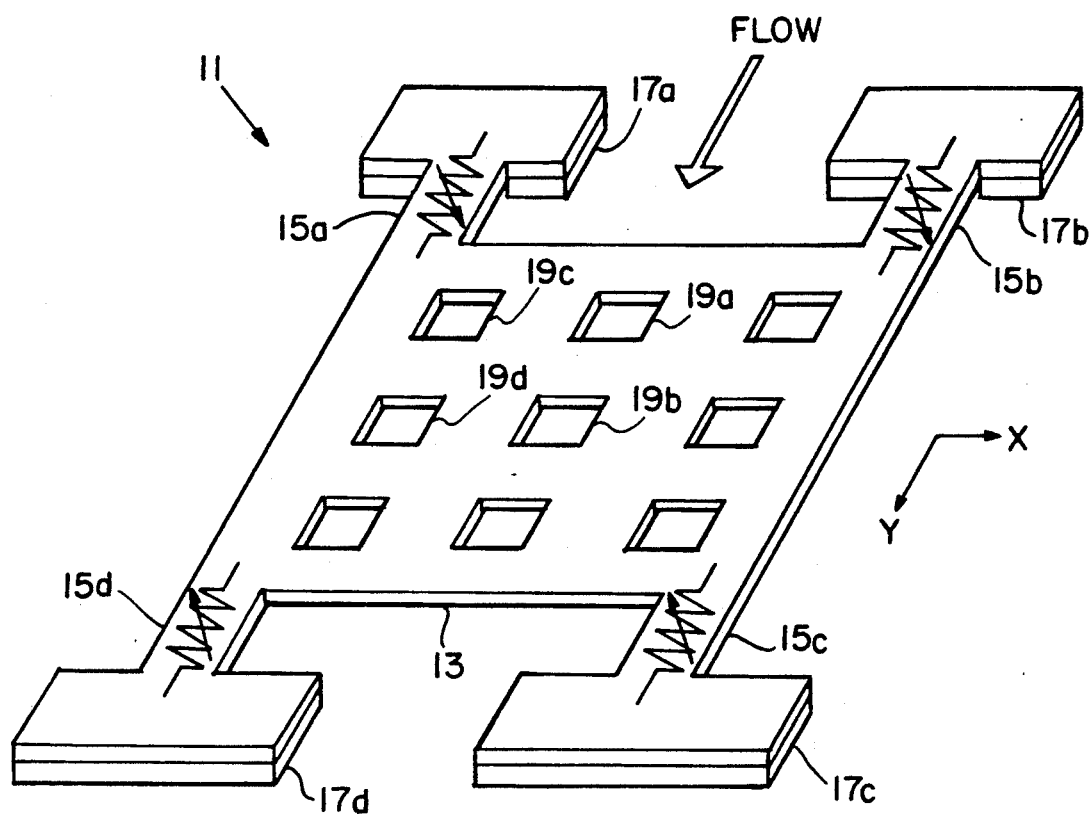
FIG. 1 is a schematic view of shear stress sensor embodying the present invention.

Illustrated in FIG. 1 is a floating element shear stress sensor 11 embodying the present invention. The sensor has a plate-like body 13 with arms 15 extending therefrom. The plate-like body 13 serves as a floating element which is suspended above a surface by arms 15.

In a preferred embodiment, plate-like body 13 comprises single crystal silicon and is dimensioned about 120 microns wide-by about 120 microns long by about 5 microns thick. Apertures 19 through the plate body 13 provide access for etchants to remove a sacrificial oxide layer described later in the fabrication process of the present invention sensor. In addition, in the preferred embodiment there are four arms 15, one extending from each corner of the plate body 13 along the y-axis illustrated in FIG. 1. Each arm comprises n-type silicon (single crystal silicon) and is about 30 microns long (along the y-axis) and about 10 microns wide (along the x-axis). At the extremity of each arm, there is a silicon dioxide base 17, the thickness of which dictates the height the arms support the plate 13 above a silicon substrate. Typically the thickness of base 17 is less than about three microns such that plate 13 is suspended above a substrate surface by about the same distance. Also, the silicon dioxide base 17 electrically insulates the sensor 11 from the silicon substrate.

Figure 6:
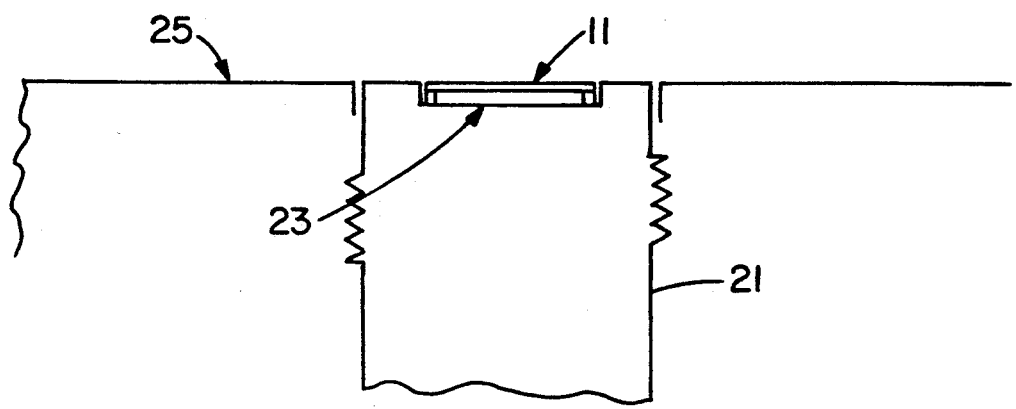
FIG. 6 is a schematic view of one application of the present invention shear stress sensor.

It is understood that other dimensions and geometric configurations of plate 13, arms 15 and bases 17 are suitable as long as plate 13 is able to lie in a plane flush with the wall of interest. FIG. 6 is illustrative where shear stress sensor 11 is schematically shown (in a side view) mounted in a cavity or a recess 23 of a device head 21. More accurately, a device head 21 is inserted (e.g. screwed) into an opening of a wall 25 of interest. Carried on the front end of device head 21 is a shear stress sensor 11 of the present invention. Sensor 11 is mounted in a cavity 23 of device head 21 such that arms 15 and bases 17 support plate 13 above the cavity floor. Thus, the cavity floor serves as a substrate surface with respect to sensor 11. The upper surface of plate 13 is preferably flush with the upper surface of the cavity side walls and is aligned flush with subject wall 25 by the controlled insertion of device head 21 in the wall opening.

Referring back to FIG. 1, the sensor 11 is positioned flush with a wall or surface of interest in a desired fluid with the longitudinal axis (y-axis) of the arms 15 parallel to the direction of flow. When the subject fluid flows over the sensor 11, a drag results and the sensor body 13 is displaced. The drag from the component of the fluid flow axial to the arms 15 (y-direction) results in compressive stresses at the pair of arms 15d, 15c farthest from the source of flow and in tensile stresses at the pair of arms 15a, 15b nearest the source of flow. Because of the crystalline nature of silicon, these stresses result in changes in resistance known as the piezoresistive effect. For the case of the n-type silicon of the preferred embodiment, compressive stresses result in an increase in resistance while tensile stresses result in a decrease in resistance, and for the same level of stress the magnitude of the change in resistance is identical.

Figure 4:
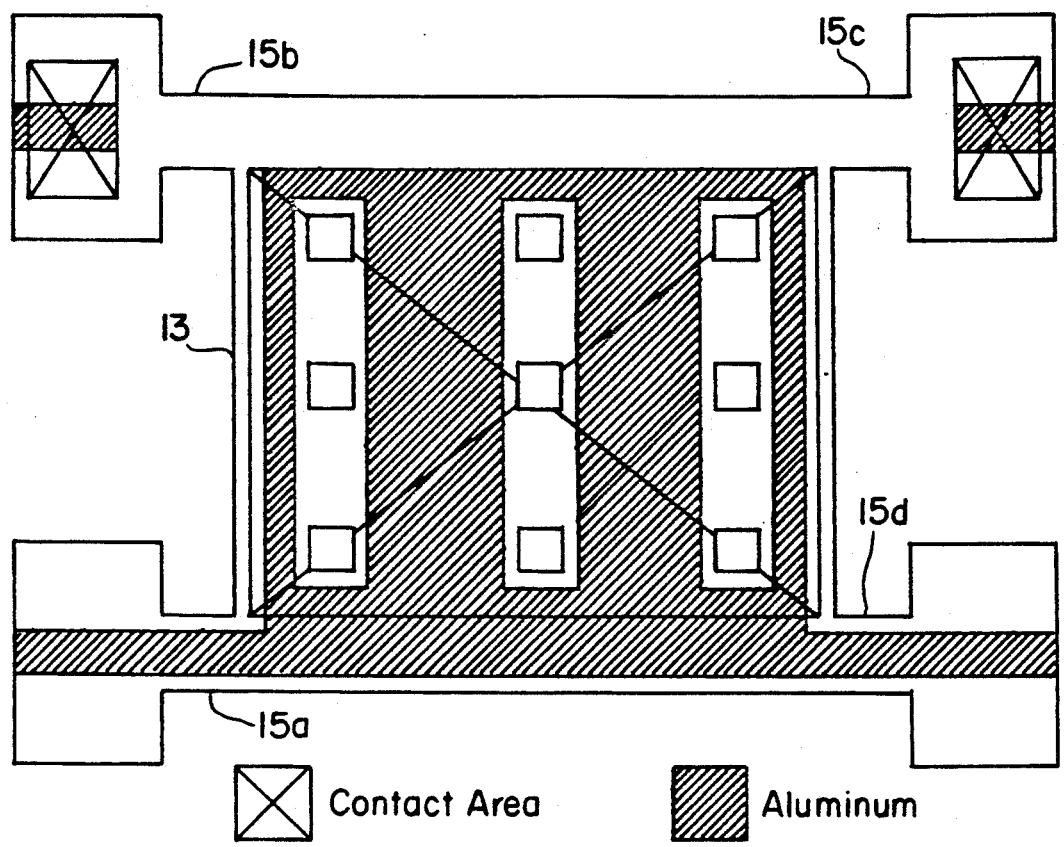
FIG. 4 is a schematic diagram of metal interconnect employed in the embodiment of FIG. 1 to support the piezoresistive measuring circuit of FIG. 2.

Thus, each of the arms 15 represent a resistor such that the electrical configuration of sensor 11 is similar to that of a Wheatstone bridge. To that end, electrical interconnects are provided at the arms 15 and plate 13 as illustrated in FIG. 4. These electrical interconnects measure the change in resistance described above and hence the shear force of the fluid flow over the target surface. It is understood that other readout means instead of electrical interconnects are suitable for measuring the change in resistance (piezoresistive effect) and hence detected shear force.

Referring to FIG. 4, the grey shaded areas are metallized portions, and the areas marked "X" are contact areas. In particular, the metal interconnect to the plate 13 is provided through one pair of arms 15a and 15d, and the resulting circuit is a half-Wheatstone bridge illustrated in FIG. 2. The plate contact serves as the sense electrode. The contact at the distal end of arm 15b serves as the drive electrode while the contact at the distal end of arm 15c (the pair mate of arm 15b) represents the ground electrode. The drive electrode provides an AC or DC voltage $V_D$ while the sense electrode detects changes in the potential $V_o$ as a function of shear stress. An advantage of using this readout configuration is its first order insensitivity to lateral (x-direction) and vertical (normal to the target surface) movements, assuming small deflections. That is, when the floating element sensor 11 is loaded (i.e., plate 13 is displaced) laterally or vertically and hence transverse to the longitudinal axis of the arms, the arms 15 undergo a change in resistance of the same magnitude and sign, thereby nulling the effect for readout purposes.

The purpose of using single crystal silicon as a material of choice stems from both its strength as a mechanical material (Young's Modulus for silicon $\approx 200$ GPa), providing sufficient rigidity for the desired applications, and the knowledge of silicon processing that has been accumulated from the field of microelectronics-fabrication. Since each arm 15 acts as a thin resistor, there is no charge leakage from the resistor to the bulk material at high temperatures as is normally the case for piezoresistors diffused into bulk silicon. It has been shown that with dielectrically isolated piezoresistors that are heavily doped, the resistors manage to attain linearity up to 300° C. without any circuit compensation. Thus, piezoresistive arms 15 provide accurate shear stress readout without limitations due to high temperature and hostile environment. In addition, the use of piezoresistors as a transduction mechanism allows the possibility of the subject liquid environment being conductive.

Accordingly, the present invention sensor 11 is designed to be robust to withstand elevated temperatures and pressures, and to be operable in conductive liquids. In particular, the preferred embodiment is able to operate in environments having the following specifications:
   viscosity of up to $10^4$ poise
   temperatures up to about 300° C.; and
   pressures of up to 10 atmospheres.
In the case of operating in conductive liquids, the present invention sensor 11 is coated with a passivation film, which insulates the piezoresistive arms 15. In addition, the floating element shear stress sensor of the present invention measures shear stresses in the range of about 1 kPa to about 100 kPa.

Figure 2:
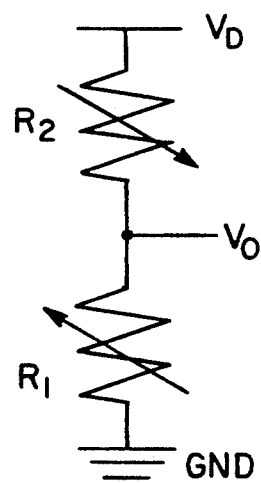
FIG. 2 is an electrical schematic diagram of a piezoresistive measuring circuit used as a read out assembly in the embodiment of FIG. 1.

As mentioned previously, by using two of the arms 15b, 15c in the sensor 11 as piezoresistors, the sensor 11 can be configured as a half Wheatstone bridge illustrated in 25 FIG. 2. One of the applied potentials to the arm 15b is biased at $V_D$, the driving voltage, and the other arm 15c is grounded. The potential $V_o$ is tapped by having metal interconnects routed to the plate body 13. When arms 15b and 15c are stressed, the resistances $R_1$ and $R_2$ change according to the following equation with the same magnitude but opposite signs.

$$\left(\frac{\Delta R}{R}\right)_\iota = G_I \epsilon_\iota \qquad \text{Equation 1}$$

where
   $G_I = \pi_{11} E + 1 + 2\nu$
   E is Young's modulus,
   $\nu$ is Poisson's ratio
   $\epsilon$ is the electric field in the $\iota$ direction and $$\pi_{11} = \pi_{111} = \frac{\partial^2 \epsilon}{\partial j_1 \partial T_{11}}$$

$j_1$ is the current density along the 1-axis; and
   $T_{11}$ is the stress in the 11 direction.
In a Wheatstone bridge configuration, the signal is a ratio of two resistors, and if the nominal resistances are identical, the signal is independent of the resistor value. On the other hand, the temperature coefficient of gauge factor (TCG) of the piezoresistors effects the output voltage and ideally, the TCG should be as small as possible. The gauge factor is reduced by increased doping in the silicon during the fabrication process of the present invention described later. A large value for the gauge factor $G_I$ is preferred. In general, for the same level of doping, and along the <100> direction, n-type silicon has higher gauge factors than p-type silicon. Furthermore, a lower level of doping increases the gauge factor but the gauge factor will be more sensitive to temperature variation for lower dopings.

In addition to the foregoing advantages, the use of single crystal silicon provides advantages over polysilicon in the fabrication of the present invention sensor. Included in these advantages are the better defined and better controlled properties of single crystal silicon in comparison to the properties of polysilicon. To that end, fabrication steps using single crystal silicon are highly repeatable which cannot be said for polysilicon. Also, polysilicon when deposited on a surface assumes the contour of that surface such that the polysilicon would fill a cavity instead of capping the cavity. In contrast, single crystal silicon when applied over a cavity forms a capping layer over the cavity, as opposed to filling the cavity, as will be made clear in the following description of the fabrication process of the present invention.

FABRICATION PROCESS

Figure 3A:
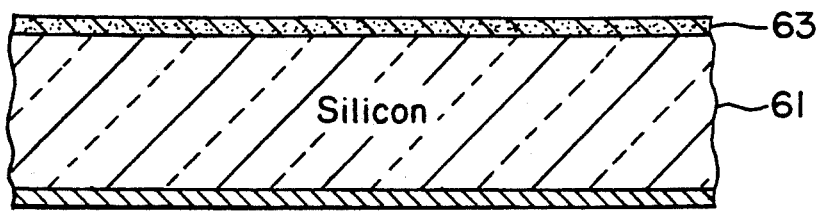
FIGS. 3a-3n illustrate the steps of the fabrication process using wafer bonding for fabricating a sensor embodying the present invention.
Figure 3B:
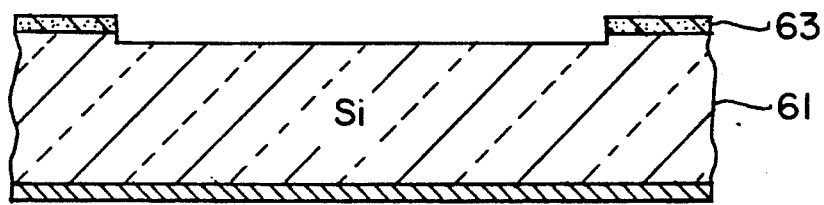
Figure 3C:
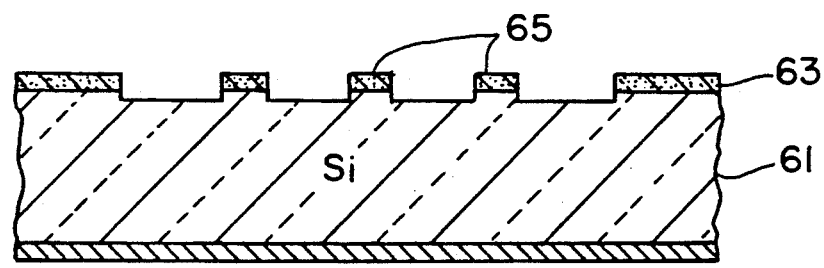
Figure 3D:
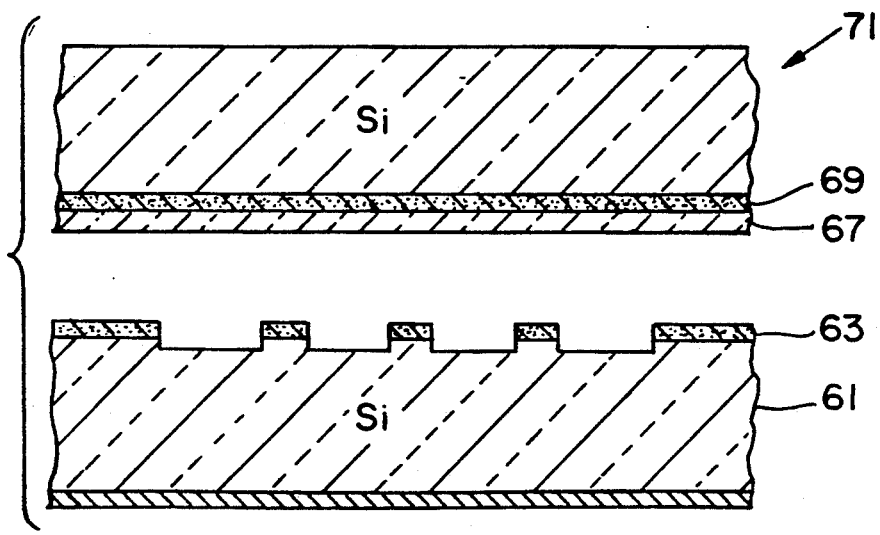
Figure 3E:
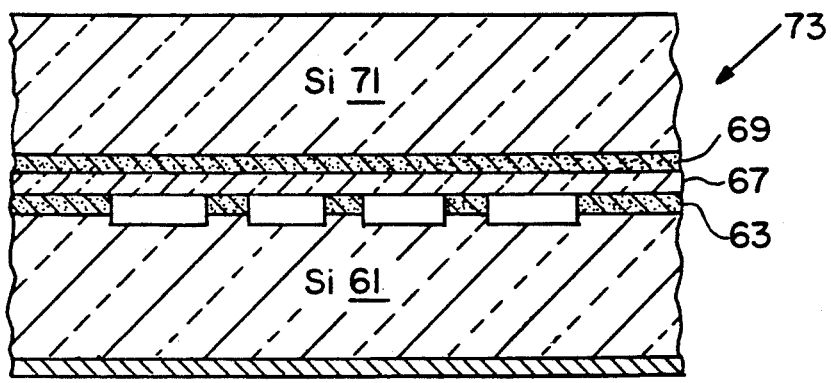
Figure 3F:
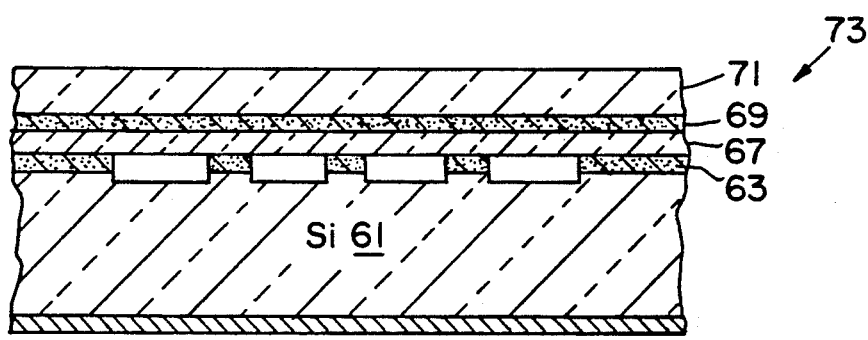
Figure 3G:
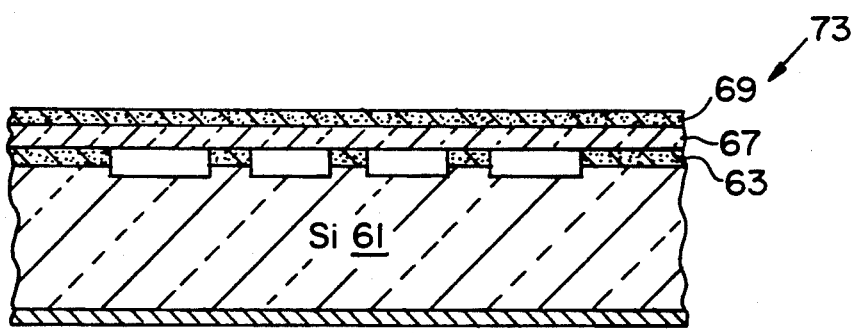
Figure 3H:
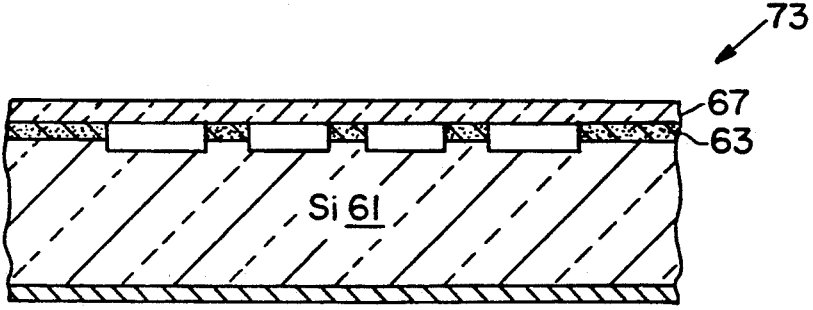
Figure 3I:
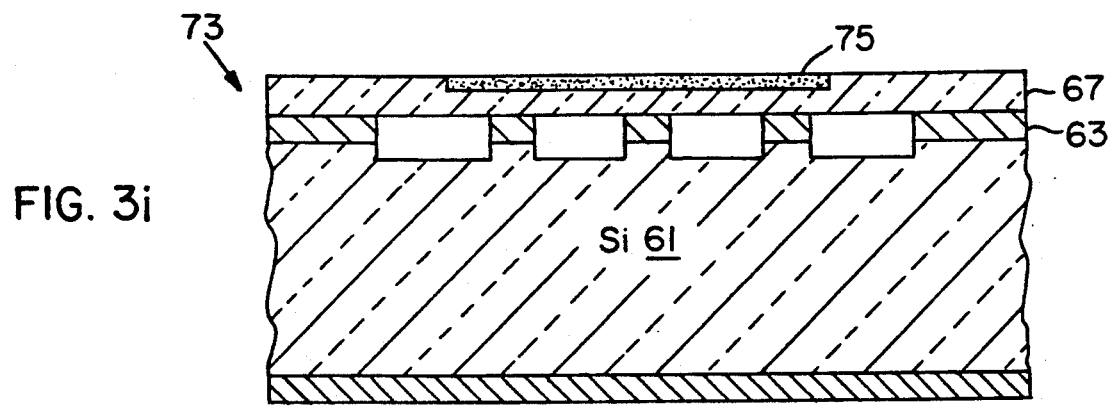
Figure 3J:
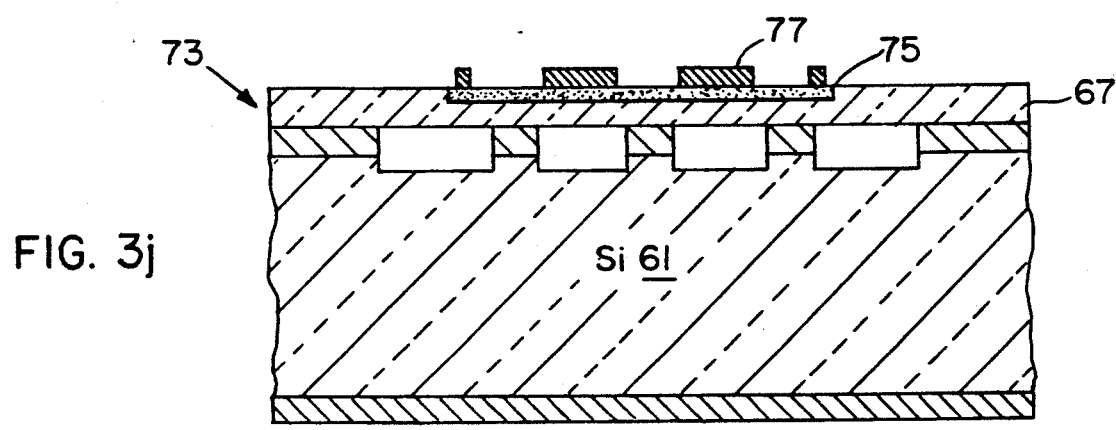
Figure 3K:
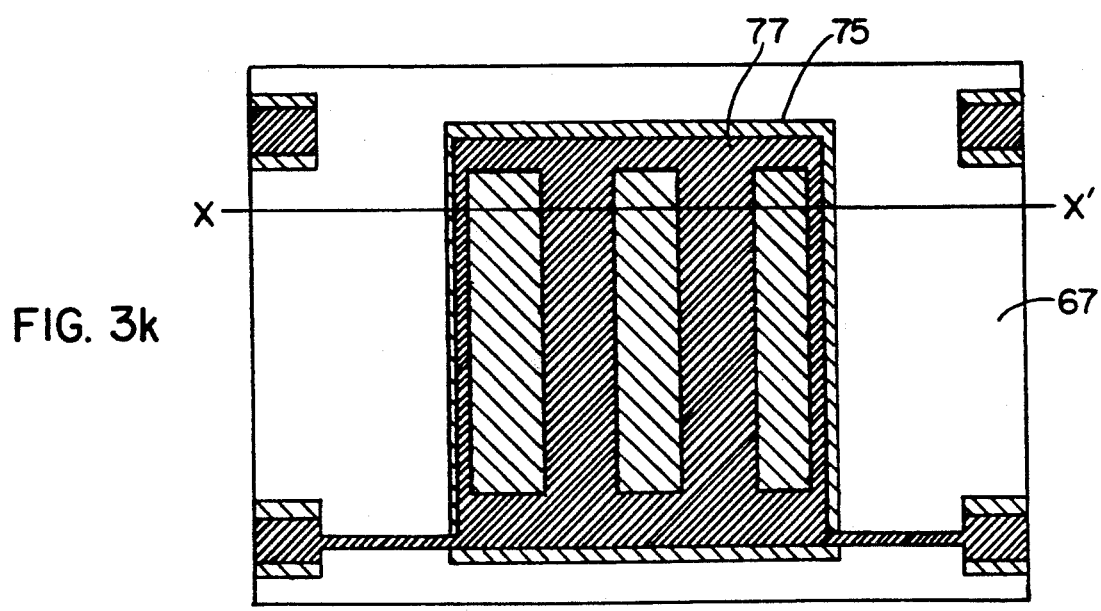
Figure 3L:
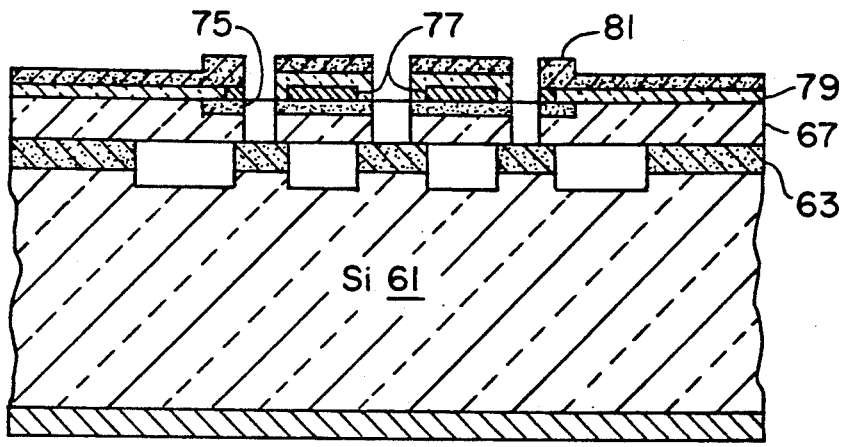
Figure 3M:
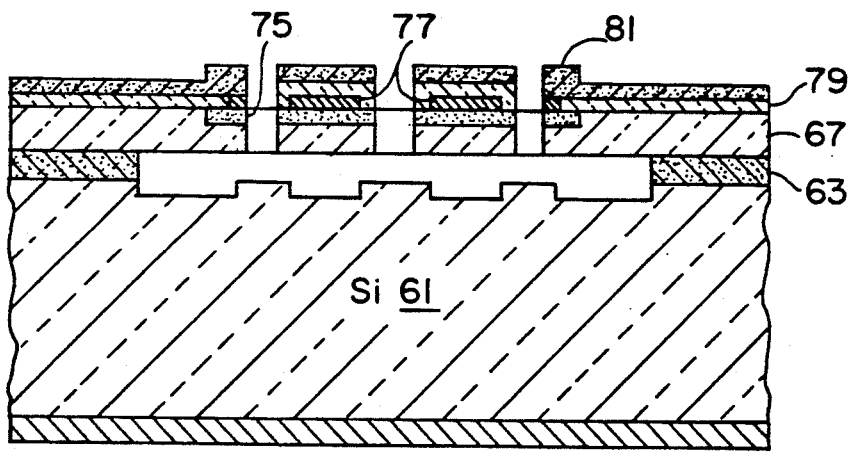
Figure 3N:
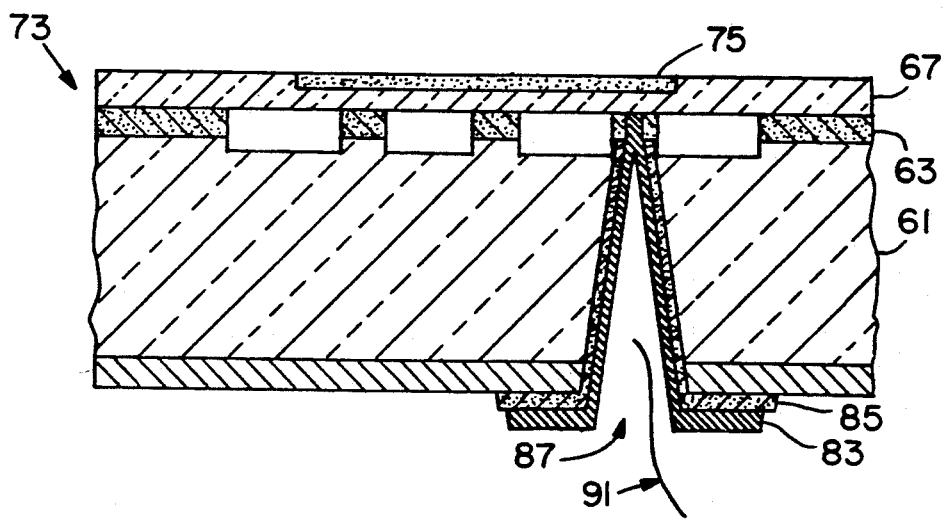

The fabrication process of the present invention sensor is illustrated in FIGS. 3a through 3n and described next. Generally two wafers are employed in the fabrication process, a first wafer which serves as a substrate and a working wafer from which the sensor body and arms are structured. For clarity and ease of understanding, in the following description, the first (substrate) wafer is referred to as the "handle wafer" 61 and the working wafer is referred to as the "device wafer" 71.

As shown in FIG. 3a the handle wafer 61 is preferably a 10-20 Ω-cm n-type <100> silicon wafer. That wafer 61 is oxidized at 950° C. in steam to thermally grow a 1.4 micron thick silicon dioxide layer 63 as shown in FIG. 3a. Using photolithography techniques, one or more windows are patterned in the oxide layer 63 on the polished side of handle wafer 61. Using a wet or dry anisotropic etch (such as a plasma etch), the oxide layer 63 is etched to open the patterned windows. The wet anisotropic etching is followed by a timed silicon plasma etch to remove about 3,000Å of exposed silicon from the polished surface of the handle wafer 61 as shown in FIGS. 3b and 3c.

FIG. 3b illustrates a single window patterned and etched in the oxide layer 63 such that all the oxide that would be under the floating element sensor is removed. In the alternative, FIG. 3c illustrates plural windows or areas patterned and etched in the oxide layer 63 such that about 90% of the oxide that would be under the sensor is removed with stumps 65 illustrated remaining. By selectively removing the oxide under the floating element sensor, the oxide etching time required to release the floating element in the final step is reduced significantly. Further, the timed plasma etch forms steps in the wafer and roughens the surface under the sensor so as to prevent sticking between the sensor and the handle wafer 61 during the release process described later.

For brevity, the plural window alternative of FIG. 3c is assumed in the following steps as illustrated in FIGS. 3d through 3m. It is understood that those steps also similarly apply to the FIG. 3b single window version although not specifically illustrated.

Next the device wafer 71 (FIG. 3d) is prepared. This includes heavily boron doping an n-type silicon wafer to form a p+ layer 69 on the front side of the device wafer 71. This p+ layer 69 is preferably about 5 to 7 microns thick and serves as an etch stop in a later described wafer thinning step. A single crystal silicon layer 67 is epitaxially grown on the p+ layer 69. The epitaxial layer 67 is preferably about 5 microns thick and is lightly doped (n-type doping) with an impurity concentration of about $10^{14}$ to $10^{15}$ cm$^{-3}$. The resulting prepared device wafer 71 is then as shown in the upper portion of FIG. 3d.

The handle wafer 61 and device wafer 71 are RCA cleaned, followed immediately by a hydration step consisting of a 10 minute immersion in 3:1 $H_2SO_4$: $H_2O_2$ without any heating. Following this the wafers 61 and 71 are dump-rinsed and spin-dried. The polished side (oxide layer 63) of the handle wafer 61 is brought into intimate contact with the front side (epitaxial layer 67) of the device wafer 71 to bond the two wafers together. Such intimate contact and bonding is made possible by the mirror smoothness of the polished side of the handle wafer 61 and the front side of the device wafer 71, and by the high concentration of OH groups on the wafer surfaces from the hydration step. That is, the mirror smoothness of the wafer surfaces allows good (a uniform) contact to be made between the two wafer surfaces, and the OH groups on the two wafer surfaces have an attraction for each other such that upon contact of the two surfaces a hydrophilic reaction takes place between the two wafers.

In the preferred embodiment, the two wafer surfaces (polished/oxide layer 63 side and front epitaxial layer 67 side) are placed in contact with each other by retaining the handle wafer 61 polished side up in a jig or other supporting assembly. The device wafer 71 is then placed with the epitaxial layer 67 side facing the handle wafer polished surface at an angle. The device wafer 71 is then released and allowed to fall and make contact with the handle wafer 61. By allowing the device wafer 71 to fall into place in a manner described above, air is expelled from between the two wafers to improve the contact made between the two wafer surfaces. A pair of tweezers are then used to press the two wafers 61, 71 firmly together and at this point, the two wafers can be handled as a pair without separating. FIG. 3e illustrates the resulting wafer pair 73.

The foregoing contacting is followed by a high temperature diffusion cycle consisting of one hour in dry oxygen at about 1,000° C. Preferably the temperature is gradually increased from 600° C. to 1,000° C. At the end of the oxidation, the temperature is gradually decreased from 1,000° C. to 800° C. before removing the wafer pair 73. This is to ensure that no large temperature gradient exists between the oxide and the furnace ambient that may result in large thermal stresses in the wafers 61, 71. After the diffusion/oxidation step, the wafer pair 73 is completely bonded.

The foregoing bonding is commonly referred to as silicon wafer (fusion) bonding. Generally such bonding is strong enough to allow plastic deformation without the two wafers 61, 71 coming apart. It is understood that additional techniques may be used to aid the bonding, such as applying an electrical field and the like.

After the handle wafer 61 and device wafer 71 have been bonded together, the device wafer 71 is chemically thinned from the back side to a thickness of about 5 microns as illustrated in FIGS. 3f through 3h. In particular, the bonded wafers are placed in polypropylene wafer cassettes and immersed in a stainless tub filled with a KOH:$H_2O$ solution. The tub is placed in a water bath with temperature control of ±0.1° C. The concentration of the KOH-water solution is 20% by weight prepared by dissolving KOH pellets in 18MΩ-cm deionized water. At this concentration, silicon has the highest etch rate for a given temperature. The temperature can be varied depending on the etch rate desired and the amount of oxide that is available to passivate the handle wafer 61.

At high temperatures, the etch rates of silicon $R_{si}$ and silicon dioxide $R_{sio2}$ increase with the ratio $R_{si}$:$R_{Sio2}$ decreasing. Therefore a thicker oxide layer 63 is required to protect the wafer at elevated temperatures. In the preferred embodiment, a temperature of 67° C. is employed, giving an etch rate of approximately 40 microns per hour. This stage of the process is a timed etch and is stopped when the device wafer 71 is 40±5 microns thick as illustrated in FIG. 3f. The thickness is measured using a CaryCompar thickness comparator (LVDT).

It is understood that other anisotropic etchants may be used in place of the KOH in the above prethinning step of FIG. 3f.

The next part of the wafer thinning process utilizes the fact that alkaline solutions exhibit reduced etch rates for heavily doped p+ silicon. Thus the p+ layer 69 can be used to stop the etching at a desired thickness. KOH has higher etch rates than CsOH but only has significantly reduced etch rates for doping greater than $10^{20}$cm$^{-3}$. CsOH, on the other hand exhibits reduced etch rates with doping greater than $10^{19}$cm$^{-3}$. As a result the above prethinning is accomplished in KOH while removal up to the etch stop is accomplished in CsOH.

In the preferred embodiment, etching to the p+ layer 69 (etch stop) is carried out in 60° C., 60% CsOH which has an etch rate of 8 microns per hour. When the p+ layer 69 is exposed to the solution, etching is significantly reduced and able to be observed visually by the absence of bubbles in these areas.

Once bubbling has ceased, indicating that the p+ layer 69 is exposed and the etch with CsOH is effectively ended, the wafer pair 73 is removed as shown in FIG. 3g.

Next a suitable chemical formula is employed to selectively remove the p+ layer 69. Specifically the wafer pair 73 is immersed in a mixture of 8:3:1 $CH_3COOH$:$HNO_3$:HF, which has a calculatable etching time. After the wafer pair 73 is immersed into the solution, the solution turns brown indicating the presence of $HNO_2$. At the end of the calculated etching time the wafer pair 73 is removed from the etchant and typically bears a brown stain. The brown stain indicates the presence of porous silicon in the lightly doped regions. To remove the brown stain (i.e., porous silicon), the wafer pair 73 is immersed in a mixture of 97:3 $HNO_3$:HF for approximately 15 seconds. Upon removal from this mixture, what remains is the lightly doped epitaxial layer 67 on about 1.4 microns of oxide layer 63 supported by the handle wafer 61 as shown in FIG. 3h.

The resulting wafer configuration 73 (FIG. 3h) is then cleaned in two rinse steps followed by an RCA cleaning. In the first rinse step, the wafer configuration 73 is rinsed in deionized water for 15 minutes. In the second rinse step, the wafer configuration 73 is rinsed in deionized water with a nitrogen bubbler for about 30 minutes.

After the above cleaning process, the wafer configuration 73 undergoes a second photolithography step which is to ion implant the wafer to form ohmic contacts. Such implantation forms low electrical resistance across sensor plate 13 which in turn makes the plate 13 a better conductor for readout purposes. An infrared aligner is used to register the implantation mask to patterned oxide layer 63. The implanted area 75 is shown in FIG. 3i in relation to the patterned oxide layer 63. The mask used for the implant is the photoresist itself and the implant is electrically activated by a high temperature anneal as described next.

The need for good ohmic contact between metal and silicon requires a region of heavily doped silicon at the metal-silicon interface. As mentioned, the doping of wafers 61, 71 is n-type and as a result the contact implant consists of arsenic at an energy of 80 keV. At this energy, the projected range is close to the surface (about 500Å). Preferably a dose of n-type dopant of about $7 \times 10^{15} cm^{-2}$ is used, making the surface heavily n-type. Masking material for the implant is prepatterned photoresist. In order to prevent overheating in the resist that may cause difficulty in removing, the wafer pair 73 is cooled using freon and the current is limited to less than 100 µA. The resist is removed using oxygen plasma in the asher.

The activation in the implants is done using a temperature cycle in the range of about 800° C. to 850° C. For arsenic implants, the wafer 73 is annealed at 850° C. in dry oxygen for one hour. Because the silicon/SiO$_2$ segregation coefficient is greater than 1, the arsenic is rejected from the oxide and is concentrated at the surface. For boron implants, activation is done at 900° C. in nitrogen for 30 minutes. Boron has a segregation coefficient of less than one and any oxide grown would be depleted at the surface and therefore, a nitrogen ambient is required.

The implant and anneal step of FIG. 3i is followed by the deposition of metal to form the interconnects. Preferably the metal used for this process is aluminum deposited at a thickness of about 5,000Å. Both sputtering (evaporation) and electron beam thin film deposition are suitable. The aluminum film 77 is patterned and etched in a photolithography step and both the cross section and plan view are shown in FIGS. 3j and 3k respectively. Preferably the aluminum layer 77 is etched in a 16:2:2:1 mixture of phosphoric acid, acetic acid, nitric acid and water respectively, and the resist is removed in the asher. The aluminum layer 77 is then sintered in nitrogen at about 375° C. for 30 minutes to form Al-Si alloy for the contacts.

Alternatively, electrical contacts may be made through the backside of handle wafer 61 as shown in FIG. 3n. In this case, holes are micromachined or otherwise formed of through handle wafer 61 from the backside to implanted region 75. This includes patterning and etching using photolithographic techniques. A conductor and necessary wiring are then inserted through the holes from the wafer backside. This includes chemical vapor deposition of a polysilicon or aluminum layer 83 over a dielectric (e.g. silicon dioxide) layer 85 on the hole walls. A conductive epoxy 87 is employed to retain wiring 91 within the dielectric and aluminum lined walls.

After the contacts are formed in FIGS. 3j and 3k, the wafer configuration 73 is dipped in 50:1 H$_2$O:HF for 20 seconds to remove any native oxide, and optionally a layer of amorphous silicon 79 is deposited over the wafer as illustrated in FIG. 3l. The purpose of the amorphous silicon layer 79 is to passivate the surface and to protect the aluminum layer 77 from etching in the release step of the floating element sensor when the wafer 73 is immersed in hydrofluoric acid. The previous removal of native oxide prevents a native oxide layer from existing between the amorphous silicon layer 79 and the single crystal silicon 67, where HF etches the native oxide and gradually attacks the metal.

Further, the amorphous silicon layer 79 protects aluminum layer 77 from corrosion where the sensor 11 is used in liquid environments. To that end, any dielectric material (e.g., silicon dioxide) may be used as a passivation layer in place of the amorphous silicon layer 79. In the preferred embodiment, the amorphous silicon 79 is deposited using a plasma enhanced chemical vapor deposition (PECVD) system. The deposition is performed with a Plasmatherm reactor using the parameters summarized in Table II. Also the amorphous silicon layer 79 when frictionally contacted with the aluminum layer 77 generates heat which diffuses the contacts to the piezoresistors.

TABLE I

| Deposition Parameters for Amorphous Silicon | |
|---|---|
| SiH$_4$ | 20 sccm |
| Frequency | 13.56 Mhz |
| Power | 10 W |
| Temperature | 220° C. |
| Throttle Press. | 350 mTorr |
| Deposition Rate | 250 Å |
| Time | about 20 minutes |

A one micron thick PECVD oxide layer 81 is then deposited over the amorphous silicon layer 79 to act as a masking material as shown in FIG. 3l. Deposition of this oxide layer 81 is also performed with a Plasmatherm but with the parameters listed in Table II.

TABLE II

| Deposition Parameters for PECVD SiO$_x$ | |
|---|---|
| SiH$_4$ | 5 sccm |
| N$_2$O | 110 sccm |
| Frequency | 13.56 Mhz |
| Power | 10 W |
| Temperature | 300° C. |
| Throttle Press. | 150 Mtorr |
| Deposition Rate | 250 Å |
| Time | about 45 minutes |

Figure 5A:
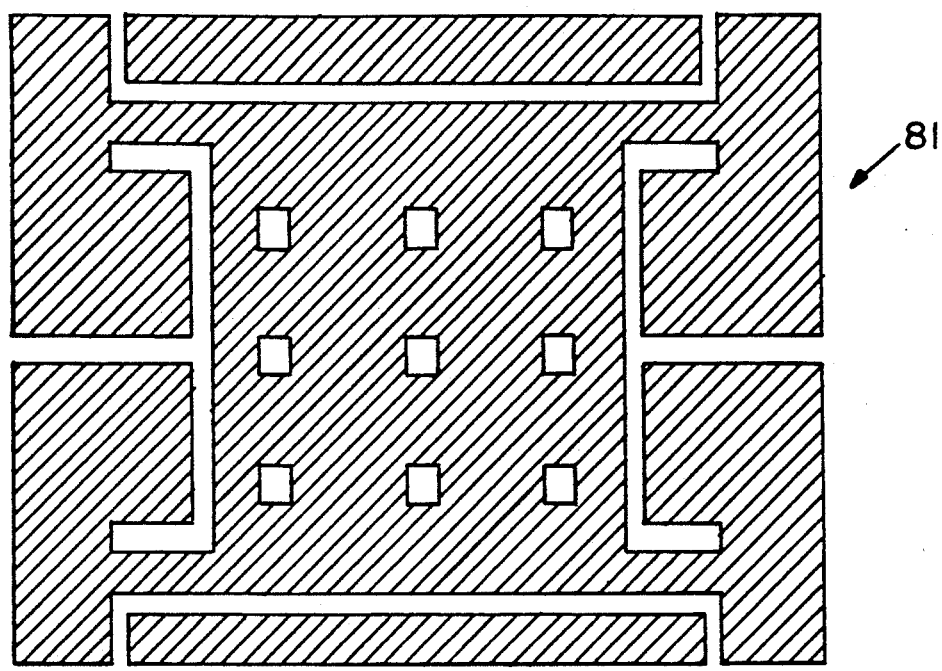
FIG. 5a illustrates a plasma etch mask used in the fabrication process of FIGS. 3a-3n.
Figure 5B:
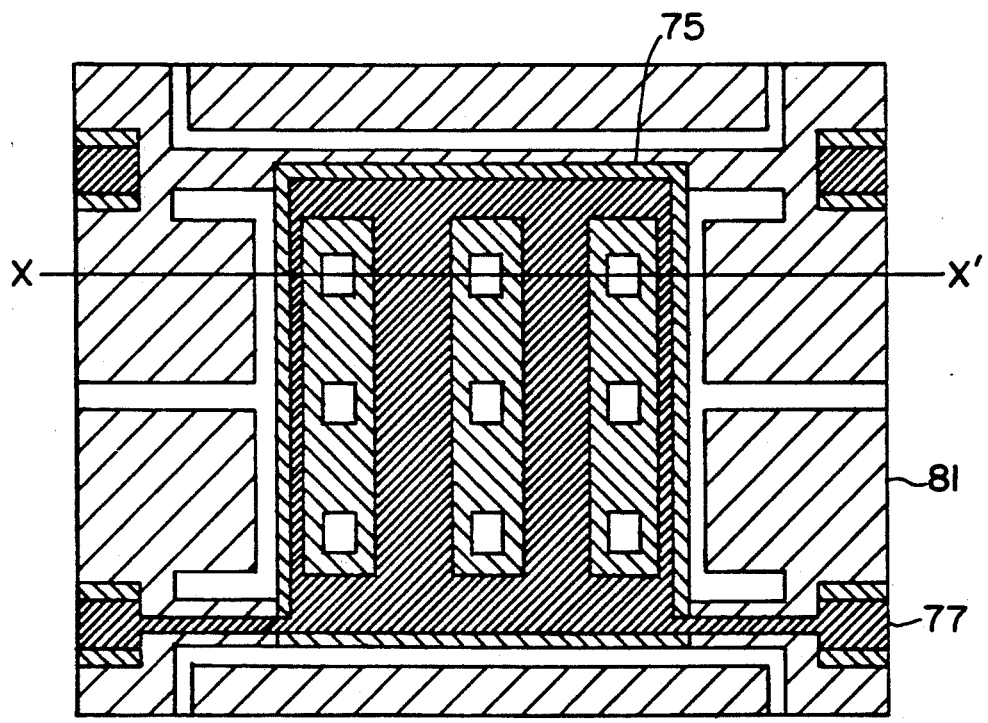
FIG. 5b illustrates layers of masks used in FIGS. 3e-3n of the fabrication process.

Next the oxide layer 81 is patterned in a photolithography step to define the floating element sensor structure. The pattern employed is shown in FIG. 5a. FIG. 5b illustrates the pattern with respect to the previous mask steps. The PECVD oxide layer 81 is then plasma etched using resist as the etch mask. Preferably the oxide plasma etch is performed in a LAM 590 etcher following the parameters of Table I above. The resist is removed in the asher. This step is followed by plasma etching of the epitaxial layer 67 with the oxide layer 81 as the mask as illustrated in FIG. 3l. This is accomplished using the silicon plasma etching described next.

In a preferred embodiment, for shallow trenches (less than about 3 microns), a SF$_6$ based plasma is used for the silicon plasma etching because of its reproducibility and high selectivity with resist. For deeper trenches a CCl$_4$ based plasma is preferred because of its minimal lateral undercutting. The foregoing silicon plasma etching are performed in a LAM 490 etcher with parameters listed in Tables III and IV. Table III the preferred parameters for the SF$_6$ based silicon etch while Table IV lists the preferred parameters for the Ccl$_4$ based silicon etch.

TABLE III

| SF₆ Silicon Plasma Etch | | | | | |
|---|---|---|---|---|---|
| | Step #1 | Step #2 | Step #3 | Step #4 | Step #5 |
| Pressure | 50 Mtorr | 450 Mtorr | 450 Mtorr | 250 Mtorr | 250 mtorr |
| RF Top | 0 | 0 W | 100 W | 0 W | 75 W |
| Gap | 1.2 cm | 1.2 cm | 1.2 cm | 1.2 cm | 1.2 cm |
| SF6 | 0 sccm | 135 sccm | 135 sccm | 100 sccm | 100 sccm |
| O₂ | 0 sccm | 45 sccm | 45 sccm | 20 sccm | 20 sccm |
| Time | Stable | Stable | Time | Stable | Overetch |

TABLE V

| Ccl₄ Silicon Plasma Etch | | | | | |
|---|---|---|---|---|---|
| | Step #1 | Step #2 | Step #3 | Step #4 | Step #5 |
| Pressure | 500 Mtorr | 500 Mtorr | 200 Mtorr | 200 Mtorr | 200 Mtorr |
| RF Top | 0 | 30 W | 0 W | 300 W | 200 W |
| Gap | 1.5 cm | 1.5 cm | 1.5 cm | 1.5 cm | 1.5 cm |
| Ccl₄ | 0 sccm | 0 sccm | 130 sccm | 130 sccm | 130 sccm |
| O₂ | 200 sccm | 200 sccm | 20 sccm | 20 sccm | 20 sccm |
| He | 100 sccm | 100 sccm | 70 sccm | 70 sccm | 130 sccm |
| Time | Stable | 6 sec | Stable | Time | Overetch |

While the etch is anisotropic, the disadvantages of the foregoing Ccl₄ etching are its reproducibility and sensitivity to wafer and etcher conditions. Sputtered material from the etcher or mask may redeposit on the wafer and inhibit etching, forming "silicon towers". This effect is known as micromasking. Finally, because the etch mechanism is mainly ion bombardment, the selectivity with respect to the mask is less favorable and for the five micron process a one micron PECVD oxide mask is preferred. The oxide mask is etched using the patterned resist as the mask and the resist is then stripped before entering the chamber for the plasma etch. Clear trenches are obtained by ensuring that the etch chamber is clean. Alternatively, the wafer may be given a short timed etch using the isotropic SF₆ etch of Table III right after the Ccl₄ etch of Table V to remove the so called "silicon towers".

At this point, processing at the wafer level is completed. Where multiple sensors are fabricated on the same wafer, the wafer is diced into individual chips accordingly, and the sensor bodies 13 (floating elements) are released as follows. In the FIG. 3b version where the oxide 63 underneath the floating element has been completely removed prior to bonding, no release step is necessary while in the FIG. 3c version, a small amount of oxide 63 remains and a release process is required. In the FIG. 3b version devices however, the alignment of the trenches to the outside pattern is critical and any offset results in asymmetry in the device and a short release step is then required to free the entire floating element.

Preferable the sensor body 13 (floating element) is released by a timed immersion of the wafer (or wafer chips) in 49% by weight HF solution, followed by a 10 minute deionized water rinse, a one minute immersion in methanol, and a drying period with a nitrogen gun. The timed etch in HF depends on the amount of oxide 63 that needs to be removed and residual stress of the silicon layer 67. The deionized water rinse is accomplished by diluting the HF solution in a cascade until all the HF is removed (about 10 minutes). This allows a gradual dilution of the HF and prevents the floating element 13 from getting stuck to the silicon handle wafer 61 due to surface tension. If the wafer 61 (or wafer chips) is withdrawn immediately from the HF solution the silicon surface dewets and the surface tension between two surfaces that are close together cause clamping. FIG. 3m illustrates in cross section along line X—X' of FIG. 5b, a successfully released sensor body 13.

To minimize the amount of undercutting, release using vapor HF is suitable. Alternatively, the thickness of the amorphous-silicon layer 79 may be made thinner (less than about 1000Å) and the conditions of the deposition may be varied to reduce the amount of stress. In the case of electrical contacts formed through the wafer backside as in FIG. 3n, the passivation layer 79 (e.g. amorphous silicon) is deposited, preferably by vapor deposition, after the release steps. Next, a method of contacting the formed contacts (FIGS. 3j, k, or n) is utilized to complete electrical contact. This includes selectively etching through the passivation layer 79 and contacting the formed contacts therethrough using common silicon fabrication techniques. Other variations and techniques may be employed in or after the release step as understood by one skilled in the art.

EQUIVALENTS

While the invention has been particularly shown and described with reference to a preferred embodiment thereof, it will be understood by those skilled in the art that various changes in form and details may be made therein without departing from the spirit and scope of the invention as defined by the appended claims.

We claim:

1. A wall shear stress sensor comprising:
   a plate having micron dimensions;
   a plurality of piezoresistive supporting arms coupled to the plate and a substrate for suspending the plate from the substrate in a plane having a subject surface over which fluid flows, each arm having a longitudinal axis, the fluid having a flow component parallel to the longitudinal axis of each arm, the arm being strained in response to fluid flow over the subject surface displacing the plate and providing an indication of deflection of the plate along the longitudinal axes of the arms; and
   readout means coupled to the plate and arms to receive the indication of deflection of the plate and to therefrom provide measurements of detected shear stress.

2. A wall shear stress sensor as claimed in claim 1 wherein the piezoresistive supporting arms are substantially insensitive to displacement of the plate along axes transverse to the longitudinal axes of the arms, such that the readout means provides measurements of shear stress substantially independent of forces acting along axes perpendicular to the longitudinal axes of the arms.

3. A wall shear stress sensor as claimed in claim 1 wherein the piezoresistive supporting arms are formed of single crystal silicon.

4. A wall shear stress sensor as claimed in claim 1 wherein the piezoresistive supporting arms are dielectrically isolated from the substrate such that the arms provide indications of plate deflection in temperatures up to about 300° C.

5. A wall shear stress sensor as claimed in claim 1 wherein the plate and arms are fabricated by the process of:
   etching a cavity into a front surface of a first silicon wafer;
   bonding a front side of a second silicon wafer to the front surface of the first silicon wafer, such that a portion of a front side of the second silicon wafer faces the cavity etched into the first silicon wafer;

thinning the second wafer from a backside opposite the front side to form a working layer suspended across the cavity in the first silicon wafer; and patterning and etching the plate and arms in the working layer in a manner such that the arms suspend the plate over the cavity in the first silicon wafer.

6. A wall shear stress sensor as claimed in claim 5 further comprising the process steps of:

forming electrical contacts to the arms; and covering the arms with a passivation layer to dielectrically isolate the arms.

7. A wall shear stress sensor as claimed in claim 6 wherein the step of forming electrical contacts to the arms includes contacting the arms through a back surface of the first silicon wafer opposite the front surface of the first silicon wafer.

8. A wall shear stress sensor as claimed in claim 1 wherein the readout means includes electrical interconnects coupled to the plate and piezoresistive supporting arms in an electrical bridge circuit configuration.

* * * * *